(12) United States Patent
Hu

(10) Patent No.: US 11,623,914 B2
(45) Date of Patent: Apr. 11, 2023

(54) CYCLIC PROCESS FOR PRODUCING TAURINE FROM MONOETHANOLAMINE

(71) Applicant: Vitaworks IP, LLC, North Brunswick, NJ (US)

(72) Inventor: Songzhou Hu, Princeton, NJ (US)

(73) Assignee: Vitaworks IP, LLC, North Brunswick, NJ (US)

( * ) Notice: Subject to any disclaimer, the term of this patent is extended or adjusted under 35 U.S.C. 154(b) by 0 days.

(21) Appl. No.: 17/576,609

(22) Filed: Jan. 14, 2022

(65) Prior Publication Data

US 2022/0135519 A1  May 5, 2022

Related U.S. Application Data

(63) Continuation of application No. 17/015,932, filed on Sep. 9, 2020, now Pat. No. 11,254,639.

(51) Int. Cl.

| C07C 303/02 | (2006.01) |
| C07C 303/44 | (2006.01) |
| C07C 303/24 | (2006.01) |
| C07C 213/08 | (2006.01) |
| C01C 1/246 | (2006.01) |
| C01C 1/247 | (2006.01) |

(52) U.S. Cl.
CPC .......... *C07C 303/44* (2013.01); *C07C 213/08* (2013.01); *C07C 303/02* (2013.01); *C07C 303/24* (2013.01); *C01C 1/246* (2013.01); *C01C 1/247* (2013.01)

(58) Field of Classification Search
None
See application file for complete search history.

(56) References Cited

U.S. PATENT DOCUMENTS

| 4,083,873 A | 4/1978 | Sherrod et al. |
| 4,597,911 A | 7/1986 | Ford et al. |
| 4,778,669 A | 10/1988 | Fuchs et al. |
| 6,077,976 A | 6/2000 | McNabb |
| 8,609,890 B1 | 12/2013 | Hu |
| 9,061,976 B1 | 6/2015 | Hu |

(Continued)

FOREIGN PATENT DOCUMENTS

| CN | 101100449 A | 1/2008 |
| CN | 102633689 A | 8/2012 |

(Continued)

OTHER PUBLICATIONS

Ma et al, "Continuous Process for the Production of Taurine from Monoethanolamine", Industrial & Engineering Chemistry Research, pp. 13007-13015, vol. 59, American Chemical Society, 2020.

(Continued)

*Primary Examiner* — Amy C Bonaparte
(74) *Attorney, Agent, or Firm* — Myers Wolin, LLC

(57) ABSTRACT

There is disclosed a cyclic process for producing taurine from monoethanolamine comprising the steps of: (a) recovering monoethanolamine sulfate from an aqueous mother liquor solution; (b) reacting the monoethanolamine sulfate with sulfuric acid to form an aqueous solution comprised of monoethanolamine bisulfate; (c) heating the aqueous solution comprised of the monoethanolamine sulfate and optionally added monoethanolamine sulfate to yield 2-aminoethyl hydrogen sulfate ester; and (d) reacting the ester with ammonium sulfite or an alkali sulfite to yield taurine.

9 Claims, 8 Drawing Sheets

(56) References Cited

U.S. PATENT DOCUMENTS

| | | |
|---|---|---|
| 9,108,907 B1 | 8/2015 | Hu |
| 9,145,359 B2 | 9/2015 | Hu |
| 9,428,450 B2 | 8/2016 | Hu |
| 9,428,451 B2 | 8/2016 | Hu |
| 9,573,890 B2 | 2/2017 | Hu |
| 9,593,076 B2 | 3/2017 | Hu |
| 9,745,258 B1 | 8/2017 | Hu |
| 9,815,778 B1 | 11/2017 | Hu |
| 9,850,200 B1 | 12/2017 | Hu |
| 9,926,265 B1 | 3/2018 | Hu |
| 9,994,517 B1 | 6/2018 | Hu |
| 10,131,621 B2 | 11/2018 | Hu |

FOREIGN PATENT DOCUMENTS

| | | |
|---|---|---|
| CN | 104998530 A | 10/2015 |
| CN | 106008280 A | 10/2016 |
| CN | 109704508 A | 5/2019 |
| JP | S608254 A | 1/1985 |

OTHER PUBLICATIONS

International Search Report with Written Opinion issued by the Federal Institute of Industrial Property of Russia, for International Patent Application No. PCT/US 2021/048814, dated Dec. 2, 2021.

International Search Report with Written Opinion issued by the Federal Institute of Industrial Property of Russia, for International Patent Application No. PCT/US 2021/048808, dated Dec. 16, 2021.

International Search Report with Written Opinion issued by the Federal Institute of Industrial Property of Russia, for International Patent Application No. PCT/US 2021/048809, dated Dec. 2, 2021.

Non-Final Office Action issued by the United States Patent and Trademark Office for U.S. Appl. No. 17/015,909, dated Jun. 15, 2021.

Final Office Action issued by the United States Patent and Trademark Office for U.S. Appl. No. 17/015,932, dated Sep. 29, 2021.

CYCLIC PROCESS FOR PRODUCING TAURINE FROM MONOETHANOLAMINE

CROSS REFERENCE TO RELATED APPLICATION

This application is a continuation of the U.S. application Ser. No. 17/015,932, filed on Sep. 9, 2020, which is incorporated herein by reference.

FIELD OF THE INVENTION

This invention relates to a cyclic process for preparing taurine from monoethanolamine through 2-aminoethyl hydrogen sulfate ester.

BACKGROUND OF THE INVENTION

Taurine can be referred to as 2-aminoethanesulfonic acid and is of the formula $H_2NCH_2CH_2SO_3H$. Taurine is an extremely useful compound because it per se has such pharmacological effects as detoxification effect, fatigue-relieving effect and nourishing and tonifying effect. As a result, taurine finds wide applications as an essential ingredient for human and animal nutrition.

Although there are numerous synthetic methods to prepare taurine and related derivatives, only two methods have been used commercially to manufacture over 60,000 tons of taurine per year, starting from ethylene oxide (the EO process) and monoethanolamine (the MEA process).

According to the EO process, EO is reacted with sodium bisulfite to yield sodium isethionate, which undergoes an ammonolysis reaction to yield a mixture of sodium taurinate, disodium ditaurinate, and trisodium tritaurinate. Neutralization with sulfuric acid results in a mixture of taurine, sodium ditaurinate, sodium tritaurinate, and sodium sulfate. The main reactions are shown in the following scheme:

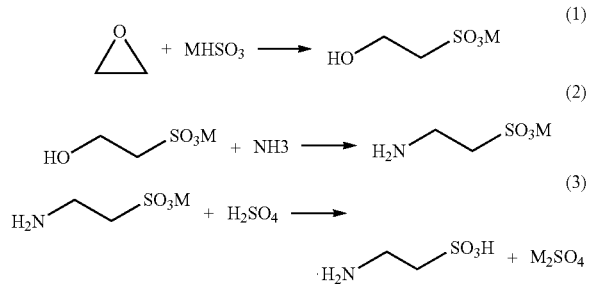

wherein M is an alkali. The alkali is lithium, sodium, potassium, or a mixture.

Although traditional EO process suffers two major problems: generation of a large amount of waste mother liquor comprised of byproducts such as sodium ditaurinate and sodium tritaurinate and the coproduction of nearly equal amount of sodium sulfate, recent processes have ameliorated these problems to reach a nearly quantitative yield and an atom efficiency.

U.S. Pat. No. 9,428,450 discloses a breakthrough finding that the byproducts of the EO process, i.e., sodium ditaurinate and sodium tritaurinate in the mother liquor solution, can be converted to sodium taurinate if they are converted to disodium ditaurinate and trisodium tritaurinate by reacting with at least equal molar amount of sodium hydroxide. This novel finding renders a cyclic process possible.

U.S. Pat. No. 9,428,451 describes a cyclic process for the production of taurine from sodium isethionate in a molar yield of at least 85% to a quantitative 100% by continuously converting the byproducts of sodium ditaurinate and sodium tritaurinate into taurine in each successive cycle.

U.S. Pat. No. 9,573,890 discloses a novel ammonolysis reaction of sodium isethionate in the presence of recycling mother liquor wherein the sodium ditaurinate and sodium tritaurinate are converted to disodium ditaurinate and trisodium tritaurinate to yield taurine in a yield of at least 85% to a quantitative 100% in one pot.

U.S. Pat. No. 8,609,890 discloses the first atom-efficient cyclic process by using isethionic acid or sulfur dioxide to neutralize alkali taurinate to produce taurine and to regenerate alkali isethionate. U.S. Pat. No. 9,108,907 further discloses a process of using isethionic acid prepared from ethanol to neutralize alkali taurinate to regenerate alkali isethionate. The aim is to reduce or eliminate the use of sulfuric acid as an acid agent in the production of taurine.

U.S. Pat. No. 9,061,976 demonstrates an integrated production scheme by using sulfur dioxide or sulfurous acid as an acid and by converting the byproducts of the ammonolysis reaction, alkali ditaurinate and alkali tritaurinate, to alkali taurinate. The overall production yield is increased to greater than 90% and the alkali sulfate is eliminated from the production process. One drawback of this process is the use of gaseous sulfur dioxide, which imparts a slight smell on the product. Another significant drawback is that the taurine product from this process may contain trace amount of alkali sulfite which could be an allergen for certain people.

U.S. Pat. Nos. 9,850,200 and 9,994,517 disclose a process for producing taurine by using an ammonium salt to react with alkali taurinate to yield taurine. In particular, ammonium bisulfite, ammonium sulfite, or their mixture is used to produce taurine and to regenerate a mixture of alkali bisulfite and alkali sulfite.

U.S. Pat. No. 9,593,076 improves the atom-efficient cyclic process disclosed in U.S. Pat. No. 8,609,890 for producing taurine from isethionic acid in an overall yield of greater than 90% to nearly quantitative, while generating no inorganic salt as byproduct. Similarly, CN 106008280A describes the use of isethionic acid to neutralize sodium taurinate and to regenerate sodium isethionate. However, the starting material, isethionic acid, is difficult to obtain commercially and is produced by a costly process of bipolar membrane electrodialysis of alkali isethionate.

U.S. Pat. Nos. 9,745,258; 9,815,778; and 9,926,265 disclose a novel atom-efficient cyclic process that replaces acids, i.e., sulfuric acid, sulfurous acid, sulfur dioxide, and isethionic acid, with ammonium isethionate to react with sodium taurinate to produce ammonium taurinate and to regenerate sodium isethionate. The ammonium taurinate is decomposed upon heating to taurine and ammonia which is recovered for the ammonolysis reaction. The regenerated sodium isethionate and recovered ammonia are then combined to produce sodium taurinate, which is further reacted with ammonium isethionate to complete the cyclic process. The cyclic process according to this novel invention is atom efficient (100% atom efficiency) and can reach a yield of nearly 100%. Since the starting material, ammonium isethionate, can be economically and conveniently prepared from ethylene oxide and ammonium bisulfite, this cyclic process becomes the most efficient and most economical. Moreover, this process yields taurine of exceptional quality. It is a foregone conclusion that this cyclic process will dominate the production of taurine in the future. The main reactions involved in this atom-efficient cyclic process can be described as follows:

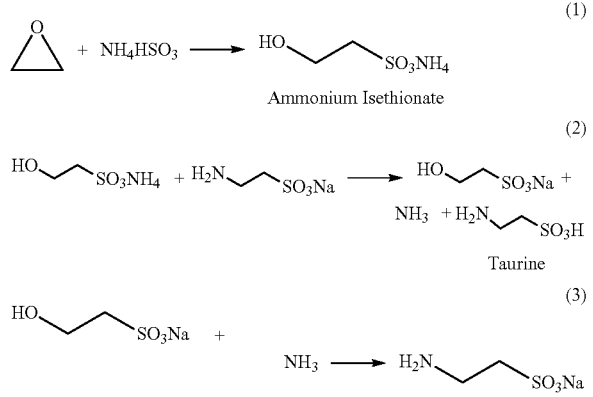

There are still disadvantages inherent in the EO process. First, taurine produced from the EO process is a powder and tends to form a hard cake over a short period of time during storage. This caking problem is alleviated significantly for taurine produced from ammonium isethionate. Second, the EO process involves some serious hazards from the viewpoint of safety since it uses, as raw material, EO, which has extremely strong toxicity and carcinogenicity and is difficult to transport and handle. Moreover, the ammonolysis reaction is carried out at high temperature (220-280° C.) and pressure (100-280 bars).

On the other hand, the MEA process uses much safer starting materials: MEA, sulfuric acid, sodium sulfite or ammonium sulfite, and milder reaction conditions (<120° C. and <2 bar) for the safe operation of the manufacturing plant. More importantly, the MEA process yields taurine of exceptional quality, a distinct advantage over the EO process. The taurine obtained from the MEA process is in the form of needle crystal and shows excellent stability during transportation and storage. It shows no sign of caking even over a long period of storage time.

According to the MEA process, taurine is produced by reacting MEA with sulfuric acid to form MEA bisulfate salt, which upon heating and removing water, is converted to 2-aminoethyl hydrogen sulfate ester (AES), the key intermediate. Subsequent reaction with a sulfite salt, for example, sodium sulfite, yields a complex mixture of taurine, sodium sulfate, sodium sulfite, and other impurities. The reactions in the MEA process can be described as follows:

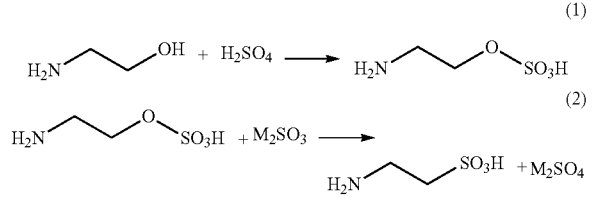

wherein M is ammonium, alkali, or a mixture. The alkali is lithium, sodium, potassium, or a mixture.

A detrimental disadvantage of the MEA process is its higher production cost over the EO process. The main cause is its much lower production yield, the most improved in the industry being in the range of 55-63%.

Attempts have been made to lower the production cost for the MEA process by substituting sodium sulfite with less costly ammonium sulfite. According to a process disclosed in JPS608254, the reaction solution of AES and ammonium sulfite is first evaporated to dry, then hydrochloric acid is added to dissolve taurine. The insoluble inorganic salt is filtered off and then washed with concentrated hydrochloric acid. Afterwards, the mother liquor is concentrated to dry again, followed by the addition of ethanol to crystallize taurine. This complicated process cannot thus be considered as an industrial production process.

According to another process described in CN101100449A, the reaction mixture between AES and ammonium sulfite is directly cooled to crystallize taurine. After filtration, the crude taurine is refined by recrystallization from distilled water. The mother liquor, comprised of taurine, ammonium sulfate, excess ammonium sulfite, and maybe other unknown organic impurities, has to be discarded.

CN102633689 describes a process of reacting AES and ammonium sulfite to produce taurine and to separate the taurine from the byproducts such as ammonium sulfate and excess sulfite with calcium hydroxide. The expensive starting material, ammonium sulfite, and valuable byproduct, ammonium sulfate, are turned into a waste mixture of calcium sulfite and calcium sulfate. In addition, residual calcium sulfate is introduced into the product stream, thus making final purification to a product of pharmaceutical grade more difficult.

U.S. Pat. No. 9,145,359 discloses a cyclic process for the production of taurine from monoethanolamine. In this cyclic process, the discharged mother liquor, comprised of monoethanolamine, ammonium sulfate, and ammonium sulfite, was reacted with excess sulfuric acid to prepare 2-aminoethyl hydrogen sulfate ester in the presence of ammonium sulfate. The process suffered several disadvantages: (1) the release of a pungent gas, sulfur dioxide; (2) the low conversion rate of monoethanolamine to the 2-aminoethyl hydrogen sulfate ester at much higher temperature than in the absence of ammonium sulfate; and (3) a turbid solution resulted from the addition of sulfuric acid to the mother liquor solution.

U.S. Pat. No. 10,131,621 discloses a process for recovering the monoethanolamine in the mother liquor solution by using an extractant. Because of the unfavorable distribution coefficient of monoethanolamine between the extractant phase and aqueous phase, the extraction process is inefficient and could not accomplish full recovery of the monoethanolamine.

The present invention discloses cyclic processes for producing taurine from MEA that overcome the disadvantages of present process, reduce the usage of starting materials such as sulfuric acid and ammonia, and produce taurine from MEA in a nearly quantitative yield.

SUMMARY OF THE INVENTION

The present invention is directed to various cyclic processes for producing taurine from monoethanolamine and intermediates thereof as recited in the claims appended hereto.

One aspect of the present invention provides a novel method for preparing MEA sulfate, an intermediate useful in the cyclic process for producing taurine, comprising reacting MEA with the ammonium sulfate in the aqueous mother liquor solution by distilling off ammonia.

Another aspect of the present invention provides a method for recovering MEA sulfate from the aqueous mother liquor solution, comprising crystallizing the ammonium or alkali sulfate in the mother liquor solution by increasing the concentration of MEA sulfate or precipitating the ammonium sulfate or alkali sulfate in the mother liquor solution with a suitable solvent and recovering MEA sulfate from the solution.

A further aspect of the present invention provides a method for recovering MEA from the aqueous mother liquor solution, comprising adding excess ammonia or alkali hydroxide to the aqueous mother liquor solution and precipitating ammonium sulfate or alkali sulfate with a suitable solvent and recovering the MEA from the solution.

The present invention discloses various embodiments of the cyclic processes that incorporate the novel methods of preparing MEA sulfate, recovering MEA sulfate, or recovering MEA from the aqueous mother liquor solution to produce taurine, comprising:

(a) reacting the prepared MEA sulfate, recovered MEA sulfate, or recovered MEA with sulfuric acid to prepare MEA bisulfate;
(b) converting the MEA bisulfate and optionally added MEA bisulfate prepared from MEA with sulfuric acid to AES by heating and removing water;
(c) subjecting the AES to a sulfonation reaction with ammonium sulfite or alkali sulfite to taurine, ammonium or alkali sulfate, and MEA sulfate byproduct;
(d) separating the taurine and the ammonium sulfate or alkali sulfate to yield an aqueous mother liquor solution comprised of dissolved ammonium sulfate and MEA sulfate;
(e) preparing MEA sulfate with the aqueous mother liquor, or recovering MEA sulfate or MEA from the aqueous mother liquor; and
(f) recycling the MEA sulfate or MEA to the next cycle as recited in step (a).

DETAILED DESCRIPTION OF THE INVENTION

The cyclic process according to the present invention starts with the reaction of MEA with ammonium sulfate in an aqueous solution to yield MEA sulfate by distilling off ammonia. This novel reaction to prepare MEA sulfate renders the cyclic process possible, because this reaction allows the use of the ammonium sulfate in the recycled mother liquor solution comprised of ammonium sulfate and MEA sulfate. Hence, the newly prepared MEA sulfate is inherently combined with the MEA sulfate in the recycled mother liquor solution to achieve an efficient and economic recycling of all MEA starting material to produce taurine.

Figure 1:
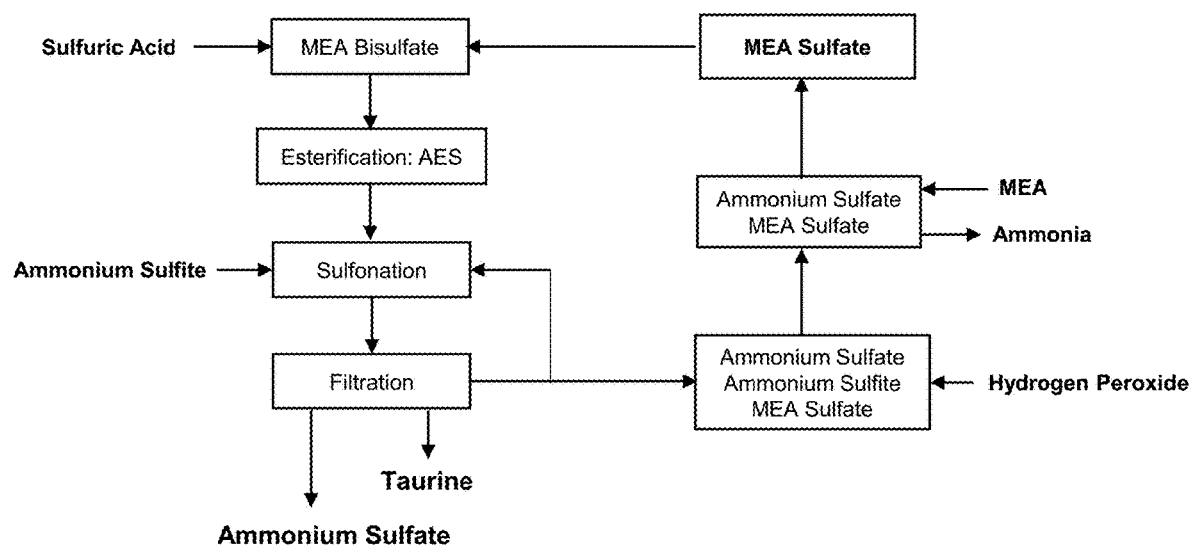
FIG. 1 is a schematic representation of a cyclic process for producing taurine by reacting sulfuric acid with the MEA sulfate prepared by reacting MEA and the ammonium sulfate in the aqueous mother liquor solution.

FIG. 1 illustrates schematically the cyclic process of producing taurine from MEA according to the present invention and the following scheme depicts the reactions in the cyclic process according to the present invention:

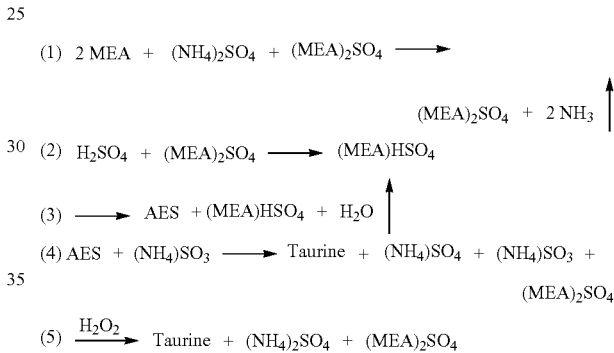

It becomes clear that the MEA sulfate and MEA bisulfate byproducts, represented in the italic bold $(MEA)_2SO_4$ and $(MEA)HSO_4$, are continuously recycled in each successive cycle after the excess ammonium sulfite $(NH_4)_2SO_3$ is converted to ammonium sulfate. Most notably, in the cyclic process according to the present invention, for every two moles of MEA, only one mole of sulfuric acid is consumed, thus greatly reducing the usage of sulfuric acid.

It is found that MEA reacts with ammonium sulfate in an aqueous solution to form an aqueous solution comprised of MEA sulfate, ammonium MEA sulfate, ammonium sulfate, MEA, and ammonia. To prepare the MEA sulfate, the ammonia is distilled off at a temperature from 50° to 150° C. under normal, reduced, or increased pressure. The molar ratio of MEA to ammonium sulfate is from 0.5 to 5.0, preferably from 1.5 to 2.5, more preferably from 1.8 to 2.2, most preferably from 1.9 to 2.1. If the ratio is greater than 2, the solution comprised of MEA sulfate is basic. If the ratio is less than 2, the solution comprised of MEA sulfate is neutral. The ammonia can be recovered and is preferably absorbed with aqueous ammonium bisulfite to prepare an aqueous solution of ammonium sulfite for the sulfonation reaction. By absorbing the ammonia with ammonium bisulfite, the cyclic process according to the present invention replaces the more expensive ammonium sulfite with ammonium bisulfite, which is also more widely available.

During the distillation of ammonia, the solution of the MEA sulfate may become discolored from straw to slightly reddish. It is found that this discolored solution can be treated with hydrogen peroxide or activated carbon to obtain a nearly colorless solution. Preferably, hydrogen peroxide is used. After the solution is treated with 1-5% by weight of hydrogen peroxide at about 80° C., the solution becomes colorless. The excess hydrogen peroxide is then decomposed at boiling temperature.

The MEA sulfate is subsequently reacted with sulfuric acid to form MEA bisulfate, an intermediate used in the reaction of MEA with sulfuric acid in the process according to the traditional MEA process. The molar ratio of MEA sulfate to sulfuric acid is from 0.1 to 5.0, preferably from 0.8 to 1.2, more preferably from 0.9 to 1.1, most preferably from 0.95 to 1.0. A little excess of sulfuric acid helps to increase the conversion rate of MEA bisulfate to AES.

The MEA bisulfate, optionally mixed with added MEA bisulfate prepared by the reaction of a new batch of monoethanolamine with sulfuric acid, is heated to yield AES by removing water. Although there are methods that can produce AES in high conversion and high yield, they are not industrially feasible. The industrial production of AES is performed by combining MEA and sulfuric acid in water and then distilling off water under vacuum. The product of AES according to this method invariably contains unreacted MEA bisulfate. Under the prevailing reaction conditions, the AES is formed in a yield of about 80% and about 20% of MEA remains unchanged (Comparative Example). If this crude product is not purified, the MEA bisulfate is neutralized and carried over to the next stage as MEA sulfate.

In the cyclic process according to the present invention, wherein the MEA sulfate is prepared from the ammonium sulfate in the mother liquor solution, the MEA sulfate and some taurine previously present in the mother liquor are inherently combined with the prepared MEA sulfate and therefore effectively recycled. However, it is not known if the taurine will inhibit the conversion of the MEA bisulfate to AES. The present inventor found that the MEA bisulfate in the presence of taurine prepared according to the present invention can be efficiently converted to AES under the disclosed conditions (Example 1 and Example 3). This finding paves the way for the successful implementation of the cyclic process according to the present invention.

In the second stage, AES undergoes a sulfonation reaction with ammonium sulfite in an aqueous solution to yield taurine and ammonium sulfate. There are two competing reactions for the AES reaction with sulfite salt in an aqueous solution: the sulfonation and the hydrolysis of the sulfate ester by the sulfite and by water, respectively. The undesirable hydrolytic reaction forms MEA bisulfate as the product as shown in the following scheme:

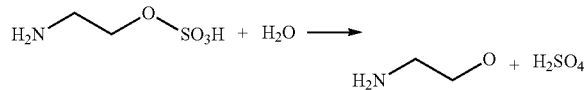

The reaction of AES with ammonium sulfite can be carried out according to the process disclosed in U.S. Pat. No. 9,145,359 to obtain a reaction mixture comprised of taurine, ammonium sulfate, excess ammonium sulfite, and MEA sulfate. The taurine and part of the ammonium sulfate can be separated from the reaction mixture by cooling, concentration, crystallization, and solid liquid separation to yield an aqueous mother liquor solution comprised of the excess ammonium sulfite, the dissolved ammonium sulfate, MEA sulfate, and a small amount of taurine.

Since the sulfonation reaction is performed at a neutral pH, MEA bisulfate from the esterification stage and the sulfonation stage is neutralized to form MEA sulfate. Hence, after the sulfonation reaction, the reaction mixture is comprised of taurine, ammonium sulfate, excess ammonium sulfite, MEA sulfate, and optionally unreacted AES.

The taurine and ammonium sulfate can be separated from the reaction mixture by methods known to one skilled in the art. For example, the reaction mixture can be cooled to crystallize taurine and the taurine is separated from the suspension by means of solid-liquid separation to give an aqueous mother liquor solution. The aqueous mother liquor solution is then concentrated to crystallize the ammonium sulfate, which is separated by means of solid-liquid to yield an aqueous mother liquor solution. Alternatively, the taurine and ammonium sulfate can be separated at the same time from the reaction mixture as a solid mixture to yield an aqueous mother liquor solution.

After the taurine and the ammonium sulfate are separated from the reaction mixture by means of solid-liquid separation, there is obtained an aqueous mother liquor solution comprised of dissolved ammonium sulfate, excess ammonium sulfite, MEA sulfate, and a small amount of taurine.

A novel aspect of the cyclic process according to the present invention is to remove the ammonium sulfite from the aqueous mother liquor solution to yield an aqueous solution comprised of ammonium sulfate and MEA sulfate. The removal of ammonium sulfite from the aqueous mother liquor solution simplifies the process and improves the quality of the product taurine, particularly with the use of an oxidant such as hydrogen peroxide, as no turbid solution is obtained.

One method to remove the ammonium sulfite is to add an acid to form an ammonium salt of the acid and to remove sulfur dioxide. The acid is selected from the group consisting of sulfuric acid, hydrochloric acid, nitric acid, phosphoric acid, hydrobromic acid, and a mixture of two or more thereof. Preferably, the acid is sulfuric acid, so that no extrinsic species is introduced to the solution.

Another method to remove the sulfite ion is to make use of a precipitating agent. The precipitating agent is selected from the group consisting of calcium chloride, calcium bromide, calcium oxide, calcium hydroxide, calcium sulfate, barium oxide, barium hydroxide, barium chloride, and a mixture of two or more thereof. Preferably, excess calcium sulfate is used to precipitate calcium sulfite and to form ammonium sulfate. The excess calcium sulfate is separated along with calcium sulfite by a solid-liquid separation method.

Furthermore, the ammonium sulfite can be removed by converting to ammonium sulfate by oxidation with an oxidant. The oxidant can be selected from the group consisting of air, oxygen, hydrogen peroxide, ammonium persulfate, sodium persulfate, potassium persulfate, sodium percarbonate, potassium percarbonate, ammonium perborate, sodium perborate, potassium perborate, sodium hypochlorite, potassium hypochlorite, and a mixture of two or more thereof. Preferably, the oxidant is air, oxygen, hydrogen peroxide, ammonium persulfate, and a mixture of two or more, so that no extrinsic species is introduced to the solution. Most preferably, the oxidant is hydrogen peroxide.

Figure 8:
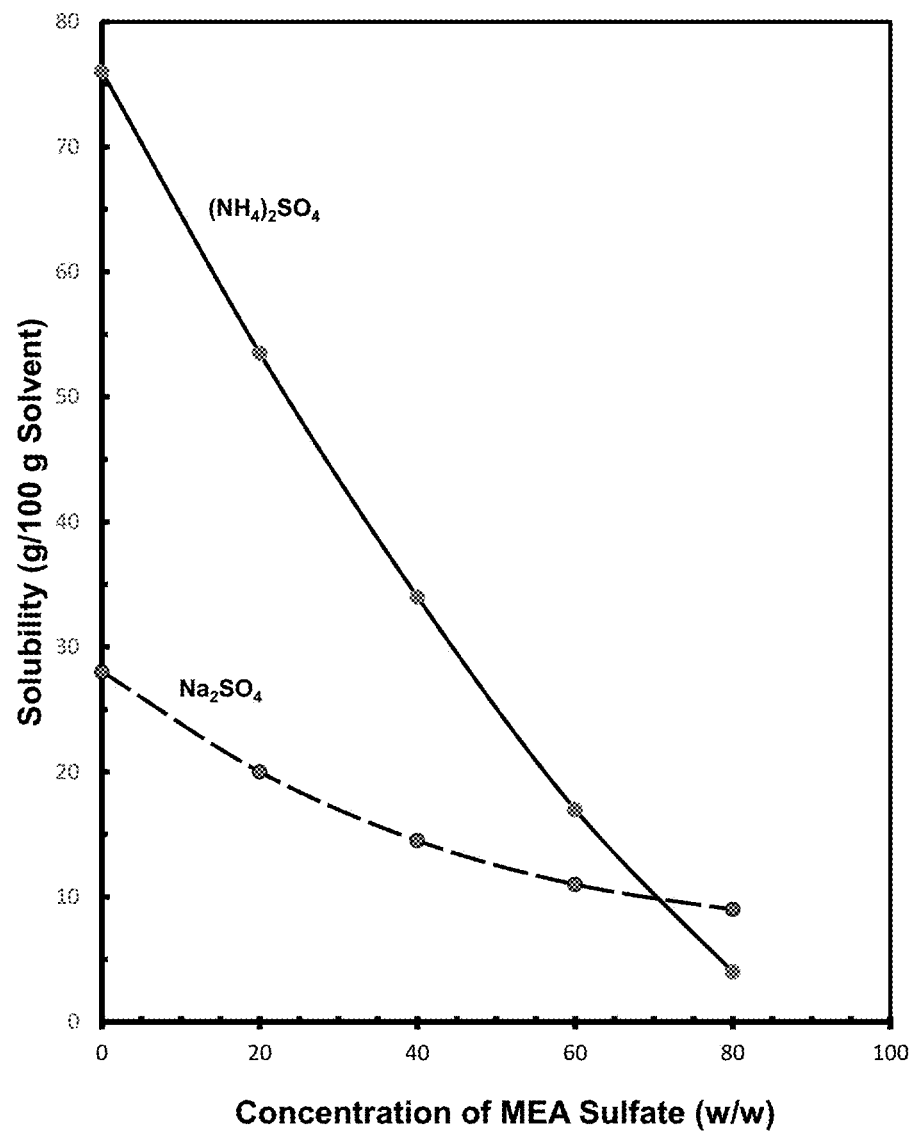
FIG. 8 shows the solubility curve of ammonium sulfate in the aqueous MEA sulfate solution.

In the cyclic process according to the present invention, the removal of the ammonium sulfite from the aqueous mother liquor solution is performed to yield an aqueous solution comprised of ammonium sulfate, MEA sulfate, some taurine. Optionally, this aqueous solution is concentrated to crystallize the ammonium sulfate and taurine, which are separated by means of solid-liquid separation. As the solution is concentrated and the MEA sulfate is enriched, the solubility of ammonium sulfate becomes less and less as shown in FIG. 8. After separation of the ammonium sulfate crystals, the solution comprised of the ammonium sulfate and the MEA sulfate is then recycled to the beginning step to react with added MEA to obtain an aqueous solution comprised of MEA sulfate by distilling off ammonia to complete the cyclic process. In the cyclic process according to the present invention, the MEA sulfate byproduct from the esterification and sulfonation reactions and taurine remained in the mother liquor are effectively recycled along with the MEA sulfate prepared from MEA to produce taurine.

The most distinct advantage of the cyclic process according to the present invention is that the MEA starting material can be fully and continuously converted to taurine in each successive cycle to achieve a nearly quantitative yield, regardless the reaction yield in each production stage.

The other advantages of the cyclic process according to the present invention become apparent: (1) the amount of sulfuric acid used is reduced by half; (2) ammonium sulfite is substituted with less expensive ammonium bisulfite; (3) the amount of ammonium sulfate generated as byproduct is reduced by half; and (4) most importantly, no waste is produced.

Figure 2:
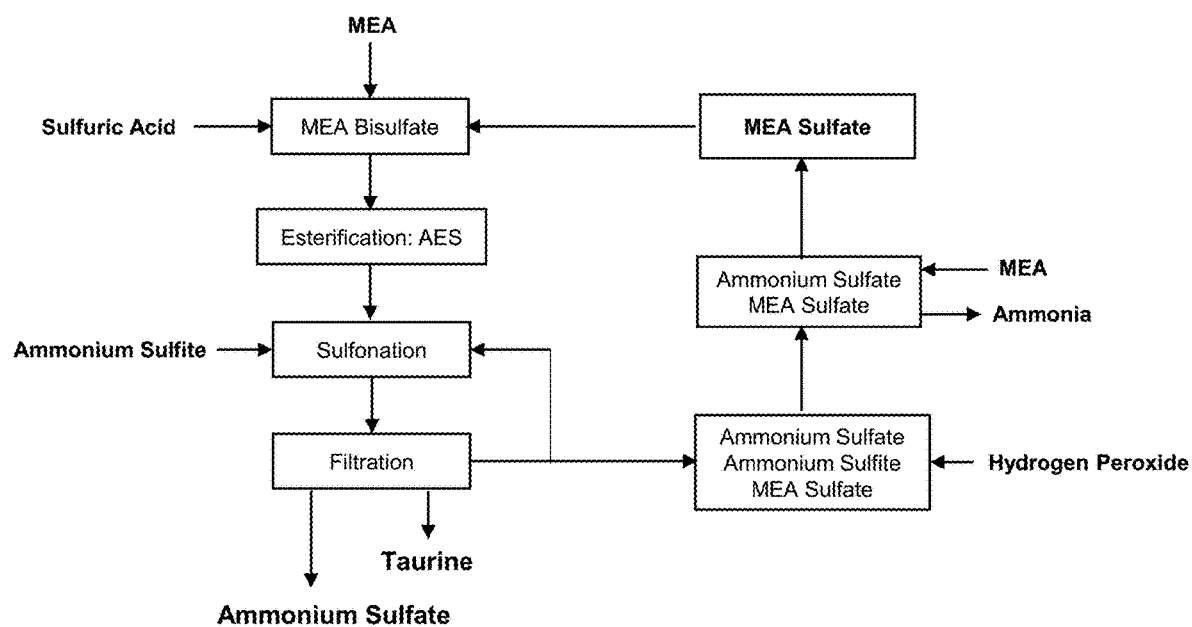
FIG. 2 is a schematic representation of a cyclic process for producing taurine by reacting sulfuric acid with MEA and the MEA sulfate prepared by reacting MEA and the ammonium sulfate in the aqueous mother liquor solution.

FIG. 2 illustrates schematically another aspect of the cyclic process according to the present invention, wherein part of the MEA is reacted with sulfuric acid to prepare MEA bisulfate, while the other part of the MEA is used to react with the ammonium sulfate in the aqueous mother liquor solution to prepare the MEA sulfate to complete the cyclic process.

In this variant of the cyclic process, the starting MEA and the recycled MEA sulfate are reacted with sulfuric acid in a nearly equal molar amount to form MEA bisulfate, which optionally mixed with added MEA bisulfate prepared by the reaction of a new batch of monoethanolamine with sulfuric acid, is heated to yield AES by removing water. The AES undergoes the sulfonation reaction with ammonium sulfite to yield taurine and ammonium sulfate. After separation of taurine and ammonium sulfate, the aqueous mother liquor is comprised of the excess ammonium sulfite, ammonium sulfate, and MEA sulfate.

One method of recycling the mother liquor solution is to continuously recycle to the sulfonation stage until the MEA sulfate in the solution becomes too high and impedes further processing. At this point, the mother liquor solution is discharged and a new cycle is started.

Another method of recycling the mother liquor is to partly recycle to the sulfonation and partly to bleed the mother liquor to keep the concentration of MEA sulfate constant so as not to impede further processing.

For both methods, the discharged mother liquor solution is comprised of the ammonium sulfate, the excess ammonium sulfite, and MEA sulfate. In the cyclic process according to the present invention, the ammonium sulfite is removed by one of the methods disclosed, preferably by oxidation with air, oxygen, hydrogen peroxide, or ammonium persulfate to yield an aqueous solution comprised of ammonium sulfate and MEA sulfate. Most preferably, hydrogen peroxide is used.

To the aqueous solution is then added MEA to afford MEA sulfate by distilling off ammonia. The aqueous solution is then cooled and reacted with sulfuric acid to form MEA bisulfate, which is optionally mixed with added MEA bisulfate prepared from the reaction of MEA and sulfuric acid and returned to the esterification stage to produce taurine.

After extensive investigation, the present inventor found some unusual properties for MEA sulfate that play an essential function for the success of the cyclic processes according to the present invention. First, MEA sulfate is an ionic liquid and does not form crystalline solid nor crystallize from the usual solvents. At room temperature, a sample containing 95% MEA sulfate and 5% water remains a liquid and does not form a solid. Second, MEA sulfate is miscible with water and certain organic solvents. This unique property is in sharp contrast to those of ammonium sulfate or alkali sulfate, which is soluble in water and insoluble in an organic solvent; Third, MEA sulfate in the aqueous solution dramatically decreases the solubility of ammonium sulfate and sodium sulfate.

These unique properties found for MEA sulfate in the instant invention render the processes of recovering MEA sulfate from the aqueous mother liquor possible, wherein the recovered MEA sulfate is particularly suitable for recycling to the process for producing taurine.

Figure 3:
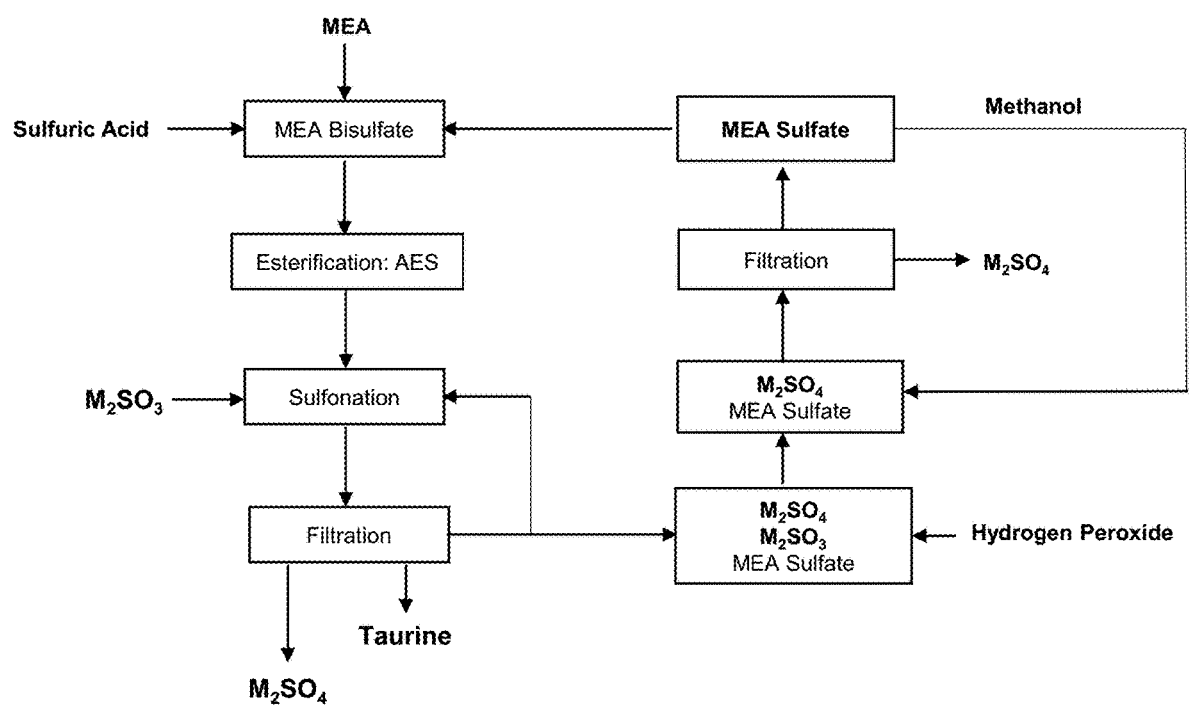
FIG. 3 is a schematic representation of a cyclic process for producing taurine by reacting sulfuric acid with MEA and the MEA sulfate recovered from the aqueous mother liquor solution with an organic solvent.

FIG. 3 illustrates schematically the embodiment of the cyclic process according to present invention, wherein the MEA sulfate in the aqueous mother liquor solution is recovered and converted to MEA bisulfate. In this embodiment of the cyclic process, the sulfonation reaction can be performed with $M_2SO_3$ in the flowchart, wherein M is ammonium, alkali, or the mixture thereof. The alkali is lithium, sodium, potassium, or the mixture thereof.

In this embodiment, the ammonium or alkali sulfite in the aqueous mother liquor solution is removed to yield an aqueous solution comprised of ammonium or alkali sulfate and MEA sulfate. This aqueous solution is optionally concentrated to further remove ammonium or alkali sulfate by crystallization and solid-liquid separation.

To the aqueous solution is then added an organic solvent to precipitate the ammonium sulfate, alkali sulfate, or the mixture. After a solid-liquid separation, the aqueous solvent solution is comprised of nearly all MEA sulfate, while the solid phase contains the sulfate salt. The aqueous solvent solution is then distilled to recover the solvent to yield an aqueous solution comprised of the MEA sulfate. Suitable solvents are found in the group consisting of methanol, ethanol, propanol, isopropanol, tert-butanol, butanol, isobutanol, sec-butanol, dimethyl carbonate, tetrahydrofuran, dioxane, and a mixture of two or more thereof. Most preferably, the solvent is methanol.

The recovered MEA sulfate is reacted with sulfuric acid to yield MEA bisulfate, which is optionally mixed with added monoethanolamine bisulfate prepared by the reaction of a new batch of monoethanolamine with sulfuric acid, and recycled to the esterification stage to AES. The AES undergoes a sulfonation reaction with ammonium or alkali sulfite to give taurine.

The MEA sulfate in the discharged mother liquor may be recovered directly without removing ammonium or alkali sulfite by adding an organic solvent to precipitate the ammonium or alkali sulfate and the excess ammonium or alkali sulfite. After a solid-liquid separation, the mother liquor is comprised of nearly all MEA sulfate, while the solid phase contains the sulfate and sulfite salt. The mother liquor is then distilled to recover the solvent to yield an aqueous solution comprised of the MEA sulfate. This MEA sulfate is reacted with sulfuric acid to yield MEA bisulfate, which is recycled to the esterification stage to produce taurine.

Figure 4:
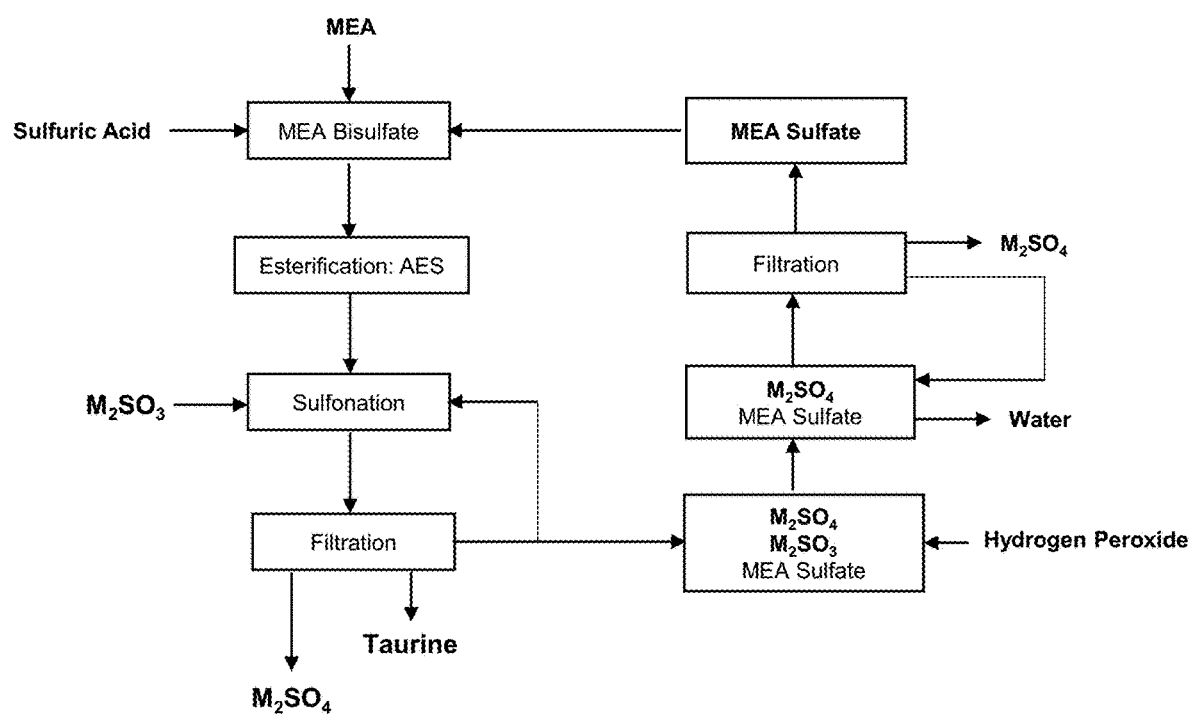
FIG. 4 is a schematic representation of a cyclic process for producing taurine by reacting sulfuric acid with MEA and the MEA sulfate recovered from the aqueous mother liquor solution by increasing the concentration of MEA sulfate.

FIG. 4 illustrates schematically the other embodiment of the cyclic process according to the present invention, wherein the MEA sulfate is recovered from the aqueous mother liquor solution without using an organic solvent and converted to MEA bisulfate to produce taurine.

Since MEA sulfate is found to dramatically decrease the solubility of ammonium sulfate and sodium sulfate as shown in FIG. 8, it is possible to isolate MEA sulfate substantially free of ammonium sulfate or sodium sulfate without using a solvent. When the concentration of MEA sulfate is 80% and greater, the solubility of ammonium sulfate becomes negligible.

To carry out the recovery of MEA sulfate from the aqueous mother liquor solution, the ammonium or alkali sulfite is preferably removed, the aqueous mother liquor solution is then repeatedly concentrated to crystallize and separate the ammonium or alkali sulfate until the aqueous solution is comprised of the MEA sulfate in a concentration of at least 50%, preferably 60%, more preferably 70%, most preferably 80% by weight/weight. Further concentration will reduce the concentration of remaining ammonium or alkali sulfate, but the solution will become too viscous for an efficient solid-liquid separation.

After separation of the crystallized ammonium or alkali sulfate, the aqueous solution comprised of MEA sulfate is particularly suitable to react with sulfuric acid to yield MEA bisulfate, which is optionally mixed with added monoethanolamine bisulfate prepared by the reaction of monoethanolamine with sulfuric acid, and then converted to AES by heating under vacuum to remove water. The residual amount of ammonium or alkali sulfate in the MEA sulfate solution thus recovered is found to have no effect on the formation of AES, either for the reaction temperature or for the yield. This finding is surprising and unexpected, since it is known from U.S. Pat. No. 9,145,359 that the presence of ammonium sulfate raises the reaction temperature of AES formation and lowers the conversion rate of MEA bisulfate to AES. The AES is then reacted with ammonium sulfite or alkali sulfite in an aqueous solution to yield taurine and ammonium or alkali sulfate.

Figure 5:
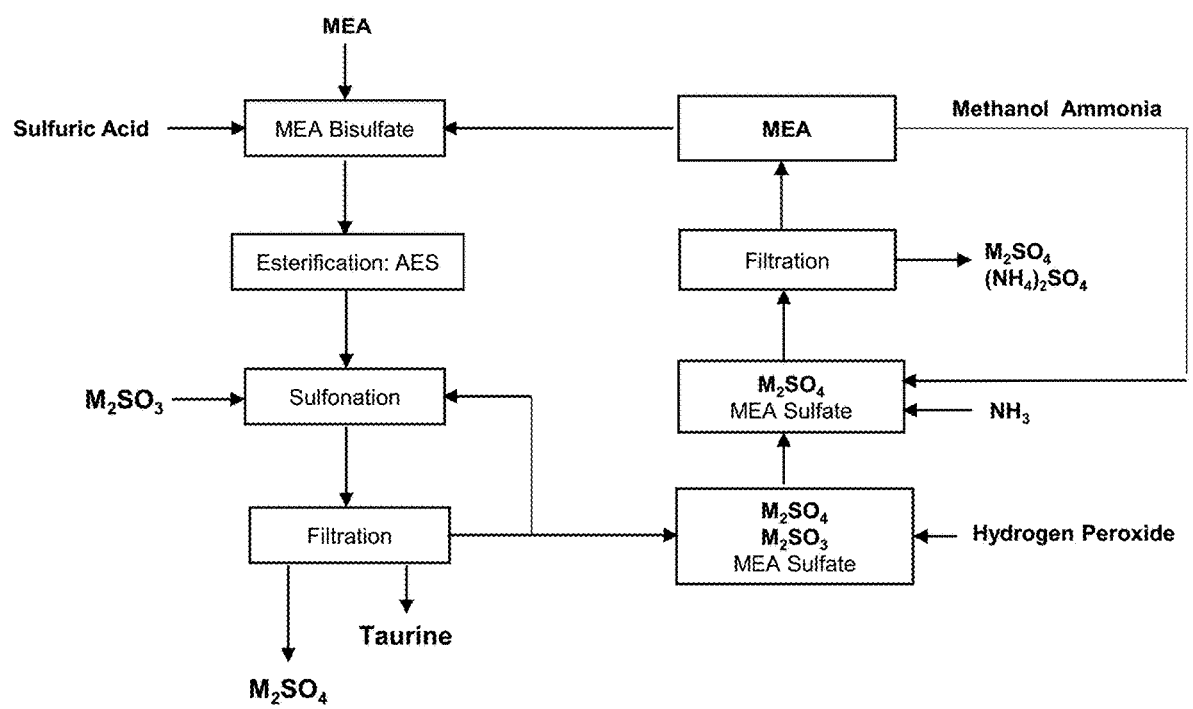
FIG. 5 is a schematic representation of a cyclic process for producing taurine by reacting sulfuric acid with MEA and the MEA recovered from the aqueous mother liquor solution with excess ammonia and an organic solvent.

FIG. 5 demonstrates a further embodiment of the cyclic process according to the present invention, wherein the MEA in the aqueous mother liquor solution is recovered and converted to MEA bisulfate. In this embodiment of the cyclic process, the sulfonation reaction can be performed with $M_2SO_3$ in the flowchart, wherein M is ammonium, alkali, or the mixture thereof. The alkali is lithium, sodium, potassium, or the mixture thereof.

It is found that when excess ammonia or ammonium hydroxide is added to the aqueous solution comprised of the MEA sulfate, followed by an organic solvent, the MEA is present in the solution while ammonium sulfate precipitates. This result is surprising and unexpected, because MEA is more basic than ammonia and MEA sulfate is soluble in the solvent or an aqueous solution of the solvent. As a result, a homogeneous solution is expected. Suitable solvents are found in the group consisting of methanol, ethanol, propanol, isopropanol, tert-butanol, butanol, isobutanol, sec-butanol, dimethyl carbonate, tetrahydrofuran, dioxane, and a mixture of two or more thereof. Most preferably, the solvent is methanol.

To the aqueous mother liquor solution comprised of $M_2SO_4$ and MEA sulfate is added excess ammonia, or ammonium hydroxide, followed by an organic solvent to precipitate $M_2SO_4$ and ammonium sulfate. An ammonia solution of the solvent may also be used to have the same effect. After a solid-liquid separation of the $M_2SO_4$ and ammonium sulfate, the aqueous solution is distilled to recover the solvent and the excess ammonia to obtain an aqueous solution comprised mainly of MEA. The solvent containing the distilled ammonia is recycled to the precipitation step. The MEA thus recovered may be used directly to prepare MEA sulfate or MEA bisulfate. Preferably, the MEA is distilled to purify and then used to produce MEA sulfate or MEA bisulfate. The recovered MEA may optionally mixed with a new batch of added MEA to produce MEA sulfate or MEA bisulfate. The residual after the distillation is MEA sulfate, which can be recycled to the process for further recovery of MEA.

Figure 6:
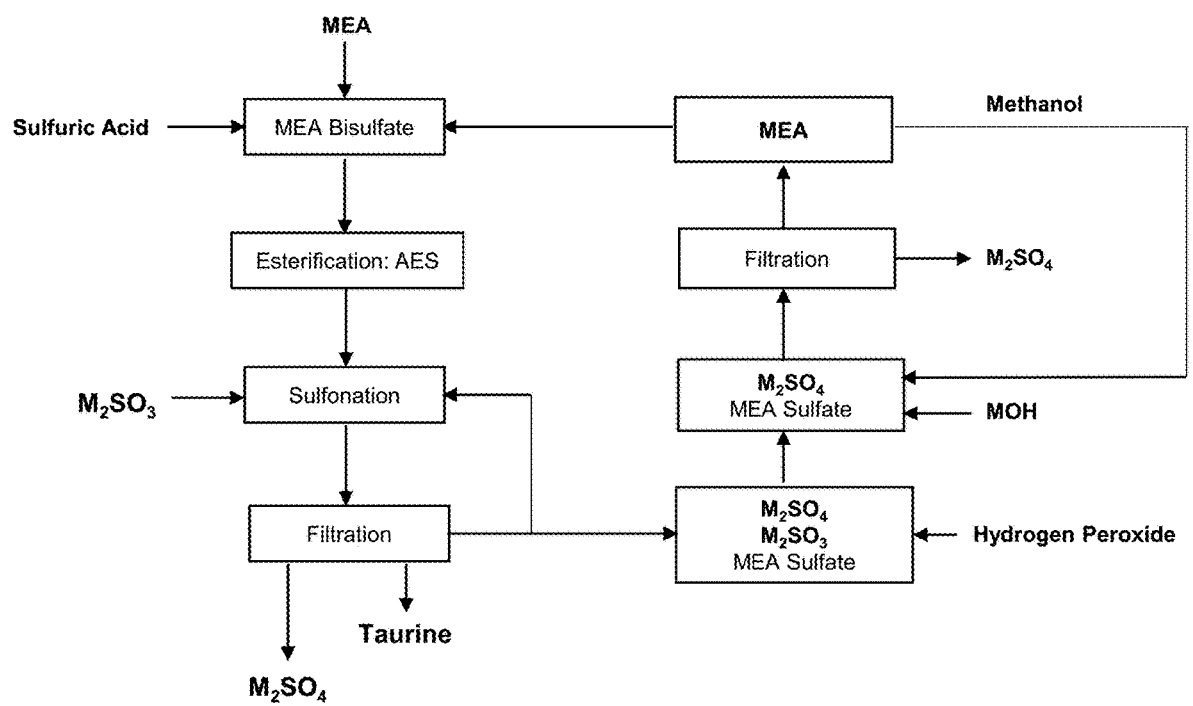
FIG. 6 is a schematic representation of a cyclic process for producing taurine by reacting sulfuric acid with MEA and the MEA recovered from the aqueous mother liquor solution with alkali hydroxide and an organic solvent.

FIG. 6 shows the use of alkali hydroxide in the further embodiment of the cyclic process according to the present invention. The cyclic process according to this further embodiment is particularly effective when an alkali sulfite is used in the sulfonation reaction.

When alkali hydroxide is added to the aqueous solution of alkali sulfate and MEA sulfate, MEA is freed from the salt and the alkali sulfate is nearly completely precipitated by an organic solvent. Suitable solvents are found in the group consisting of methanol, ethanol, propanol, isopropanol, tert-butanol, butanol, isobutanol, sec-butanol, dimethyl carbonate, tetrahydrofuran, dioxane, and a mixture of two or more thereof. Most preferably, the solvent is methanol. The high efficiency is due to the fact that MEA is a much weaker base than alkali hydroxide.

To the aqueous mother liquor solution comprised of alkali sulfate and MEA sulfate is added an alkali hydroxide, preferably, sodium hydroxide, followed by an organic solvent, preferably methanol to precipitate alkali sulfate. After a solid-liquid separation of the alkali sulfate, the aqueous solution is distilled to recover the solvent to obtain an aqueous solution comprised of the MEA and some excess alkali hydroxide. The MEA is preferably distilled to purify and then used to produce MEA sulfate or MEA bisulfate. The recovered MEA may optionally mixed with a new batch of added MEA to produce MEA sulfate or MEA bisulfate. The distillation residue is the excess alkali hydroxide, which can be recycled to the process.

It is also possible to use an alkaline oxide or an alkaline hydroxide to precipitate the alkaline sulfate, especially if ammonium sulfite is used in the sulfonation reaction. The alkaline is calcium, barium, or their mixture. Because calcium sulfate and barium sulfate are insoluble in water, it is not necessary to use a solvent to precipitate them. But the use of a solvent may be beneficial. When an alkaline oxide or an alkaline hydroxide is added to the aqueous mother liquor solution, a solid precipitate is obtained. After a solid-liquid separation of the solid comprised of alkaline sulfate, an aqueous ammonia solution of MEA is obtained. After distillation to remove ammonia, this solution may be used directly for the production of MEA sulfate or MEA bisulfate. Preferably, the MEA is purified by distillation. The recovered MEA may optionally mixed with a new batch of added MEA to produce MEA bisulfate, which is recycled to produce taurine.

Figure 7:
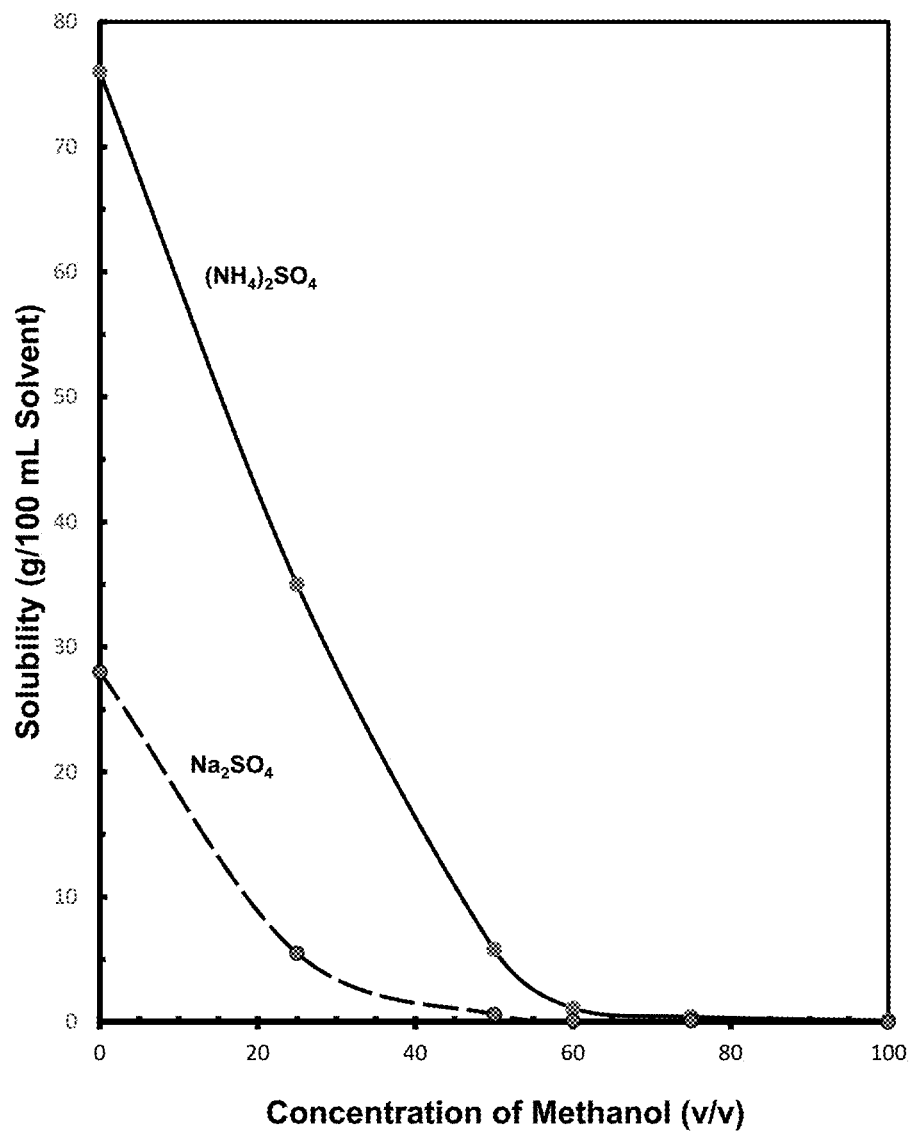
FIG. 7 shows the solubility curve of ammonium sulfate and sodium sulfate in the aqueous methanol solution.

FIG. 7 illustrates the solubility curve of ammonium sulfate and sodium sulfate in the aqueous methanol solution. It becomes clear that the solubility of either ammonium sulfate or sodium sulfate is negligible for a solution containing more than 50% (v/v) methanol. The low solubility of ammonium sulfate or sodium sulfate renders their separation from soluble components such as MEA sulfate or MEA effective and efficient.

Although it is preferable to remove the ammonium sulfite or the alkali sulfite in the aqueous mother liquor in the cyclic processes according to the present invention, it is also possible to perform the cyclic processes without removing the sulfite, particularly for the cyclic processes illustrated in the FIG. 3, FIG. 4, FIG. 5, and FIG. 8. In these cases, the salts precipitated from the aqueous solution will be a mixture of sulfite and sulfate.

EXAMPLES

The following examples will illustrate the practice of this invention but are not intended to limit its scope.

Comparative Example 61.0 g of MEA was diluted with 100 mL of water and added to 200 mL of aqueous solution containing 101.0 g of sulfuric acid, while maintaining the temperature<50° C. The solution containing the MEA bisulfate was divided into two equal parts.

One part of the solution was placed in a 500-mL flask and was stirred and heated on an oil bath under vacuum to distill the water. The oil bath was kept at 130°–145° C. until the solution became semi-solid and could not be stirred. The solid was kept at the same temperature for an additional 15 minutes under vacuum. The solid product was dissolved in about 1000 mL of water and analyzed for AES and MEA contents by HPLC. The procedure yielded the AES in a yield of 78% and 22% of MEA remained unchanged.

Example 1

The same experiment as Comparative Example was performed for the other part of the solution, to which 12.15 g of taurine was added. Nearly the same phenomenon was observed as for the reaction in the absence of taurine. HPLC showed that the procedure yielded the AES in a yield of 79% and 21% of MEA remained unchanged.

Example 2

61.0 g of MEA (1.0 mol) and 66.5 g of ammonium sulfate (0.5 mol) were dissolved in 250 mL of deionized water in a 1-L flask. The solution was distilled to a temperature of 105° C. At this point, the distillate became neutral and the solution in the flask became neutral at a pH 7 and was comprised of MEA sulfate. After the solution was cooled to room temperature, 51 g of sulfuric acid was added to the solution to prepare the MEA bisulfate. The solution was divided into two equal parts.

One part of the MEA bisulfate solution was stirred and heated on the oil bath at 130°–145° C. under vacuum to distill water until the solution became solid. The solid material was dissolved in 500 mL of water and analyzed for AES and MEA contents. The procedure yielded the AES in a yield of 74% and 26% of MEA remained unchanged.

Example 3

To the other part of the MEA bisulfate solution prepared in Example 2 was added 12.5 g of taurine and the solution was stirred and heated on the oil bath at 130°–145° C. under vacuum to distill water until the solution became solid. The solid material was dissolved in 500 mL of water and analyzed for AES and MEA contents. The procedure yielded the AES in a yield of 75% and 25% of MEA remained unchanged.

Example 4

To 500 mL of the aqueous mother liquor solution obtained according to U.S. Pat. No. 9,145,359 was added slowly 70 mL of 35% hydrogen peroxide, while the temperature was maintained at 50° C. until the sulfite was no longer present. The solution was concentrated to the appearance of ammonium sulfate crystals and cooled to the room temperature. The suspension was filtered to remove the crystalized ammonium sulfate to obtain an aqueous solution comprised of 68 g of ammonium sulfate, 76 g of MEA sulfate, and 7.6 g of taurine.

To the aqueous mother liquor solution was added 63.0 g of MEA and the solution was distilled until the temperature inside the flask reached 105° C. At this point, both the distillate and the solution in the flask were slight basic. After cooling to room temperature, 140 g of sulfuric acid was carefully added to the aqueous solution to prepare an aqueous solution comprised of monoethanolamine bisulfate.

The monoethanolamine bisulfate in the aqueous solution was converted to the AES according to Example 3. HPLC analysis showed that 75% of MEA is converted to AES and 25% of MEA remained unchanged on a molar basis.

Example 5

To 500 mL of the aqueous mother liquor solution obtained according to U.S. Pat. No. 9,145,359 was added slowly 70 mL of 35% hydrogen peroxide, while the temperature was maintained at 50° C. until the sulfite was no longer present. The solution was concentrated to the appearance of ammonium sulfate crystals and cooled to the room temperature. The suspension was filtered to remove the crystalized ammonium sulfate to obtain an aqueous solution comprised of 72 g of ammonium sulfate, 76 g of MEA sulfate, and 7.6 g of taurine.

To the aqueous solution was slowly added 300 mL of methanol to obtain a crystalline suspension. After the suspension was stirred and cooled to 10° C., it was filtered and the filtrate cake was washed with 100 mL of methanol containing 5% of ammonium hydroxide. The solid ammonium sulfate was dried and weighted 61.0 g. The mother liquor solution was distilled to recover methanol and to obtain an aqueous solution comprised of 76 g of MEA sulfate, to which 38.0 g of sulfuric acid was added to form MEA bisulfate.

The monoethanolamine bisulfate in the aqueous solution was converted to the AES according to Example 3. HPLC analysis showed that 69% of MEA is converted to AES and 31% of MEA remained unchanged on a molar basis.

Example 6

To 600 mL of the aqueous mother liquor solution obtained according to U.S. Pat. No. 9,145,359 was added slowly 85 mL of 35% hydrogen peroxide, while the temperature was maintained at 50° C. until the sulfite was no longer present. The solution was concentrated to the appearance of ammonium sulfate crystals and cooled to the room temperature. The suspension was filtered to remove the crystalized ammonium sulfate to obtain an aqueous mother liquor solution. The aqueous mother liquor solution was concentrated to crystallize and separate ammonium sulfate two more times. There was obtained 108 g of a final mother liquor solution comprised of 88.0 g of MEA sulfate.

To the solution was added 39.8 g of sulfuric acid to form MEA bisulfate, which was heated at 135° to 145° C. under vacuum distillation to form a solid AES according to Example 3. HPLC analysis showed that 86% of MEA is converted to AES and 14% of MEA remained unchanged on a molar basis.

Example 7

To 500 mL of the aqueous mother liquor solution obtained according to U.S. Pat. No. 9,145,359 was added slowly 70 mL of 35% hydrogen peroxide, while the temperature was maintained at 50° C. until the sulfite was no longer present. The solution was concentrated to the appearance of ammonium sulfate crystals and cooled to the room temperature. The suspension was filtered to remove the crystalized ammonium sulfate to obtain an aqueous solution comprised of 69 g of ammonium sulfate, 76 g of MEA sulfate, and 7.6 g of taurine.

To the aqueous solution was added 100 mL aqueous solution of 25% ammonia and 400 mL of methanol to obtain a suspension. After the suspension was stirred and cooled to 10° C., it was filtered and the filtrate cake was washed with 100 mL of methanol containing 5% of ammonium hydroxide. The solid ammonium sulfate was dried and weighted 104.5 g. The mother liquor solution was distilled to recover methanol and ammonia to obtain an aqueous solution comprised of 21 g of MEA, to which 38.0 g of sulfuric acid was added to form MEA bisulfate.

The monoethanolamine bisulfate in the aqueous solution was converted to the AES according to Example 3. HPLC analysis showed that 69% of MEA is converted to AES and 31% of MEA remained unchanged on a molar basis.

It will be understood that the foregoing examples, explanation, and drawings are for illustrative purposes only and that in view of the instant disclosure various modifications of the present invention will be self-evident to those skilled in the art. Such modifications are to be included within the spirit and purview of this application and the scope of the appended claims.

What is claimed is:

1. A process for recovering monoethanolamine sulfate from an aqueous mother liquor solution comprised of monoethanolamine sulfate and at least one additional component selected from the group of inorganic salts consisting of ammonium sulfate, ammonium sulfite, alkali sulfite, alkali sulfate, and a mixture thereof, wherein the alkali is lithium, sodium, potassium, or a mixture, said process comprising:
   (a) adding a solvent to an aqueous mother liquor solution, to precipitate the inorganic salts;
   (b) separating the inorganic salts by solid-liquid separation to yield a solution comprised of the monoethanolamine sulfate; and
   (c) distilling off the solvent from the solution of step (b) to yield an aqueous solution comprised of the monoethanolamine sulfate.

2. The process of claim 1, wherein the solvent is selected from the group consisting of methanol, ethanol, propanol, isopropanol, tert-butanol, butanol, isobutanol, sec-butanol, dimethyl carbonate, tetrahydrofuran, dioxane, and a mixture thereof.

3. The process according to claim 1, wherein the solvent is methanol.

4. A process for producing taurine, comprising:
   (a) adding a solvent to an aqueous mother liquor solution comprised of monoethanolamine sulfate and at least one additional component selected from the group of inorganic salts consisting of ammonium sulfate, ammonium sulfite, alkali sulfite, and alkali sulfate, to precipitate the inorganic salts, wherein the alkali is lithium, sodium, potassium, or a mixture;
   (b) separating the inorganic salts by solid-liquid separation to yield a solution comprised of the monoethanolamine sulfate;
   (c) distilling off the solvent from the solution of step (b) to yield an aqueous solution comprised of the monoethanolamine sulfate;
   (d) adding sulfuric acid to the aqueous solution comprised of the monoethanolamine sulfate of step (c) to form monoethanolamine bisulfate;
   (e) heating the aqueous solution comprised of the monoethanolamine bisulfate of the step (d) to yield 2-aminoethyl hydrogen sulfate ester;
   (f) reacting the 2-aminoethyl hydrogen sulfate ester of step (e) with a sulfite salt in an aqueous solution to yield taurine, wherein the sulfite salt is selected from the group consisting of ammonium, lithium, sodium, potassium, and a mixture thereof; and
   (g) separating the taurine of step (f) by solid-liquid separation.

5. The process of claim 4, wherein the solvent is selected from the group consisting of methanol, ethanol, propanol, isopropanol, tert-butanol, butanol, isobutanol, sec-butanol, dimethyl carbonate, tetrahydrofuran, dioxane, and a mixture thereof.

6. The process of claim 4, wherein the solvent is methanol.

7. A process for producing taurine, comprising:
   (a) adding a solvent to an aqueous mother liquor solution comprised of monoethanolamine sulfate and at least one additional component selected from the group of inorganic salts consisting of ammonium sulfate, ammonium sulfite, alkali sulfite, and alkali sulfate, to precipitate the inorganic salts, wherein the alkali is lithium, sodium, potassium, or a mixture;
   (b) separating the inorganic salts by solid-liquid separation to yield a solution comprised of the monoethanolamine sulfate;
   (c) distilling off the solvent from the solution of step (b) to yield an aqueous solution comprised of the monoethanolamine sulfate;
   (d) mixing the aqueous solution of step (c) with additional monoethanolamine;
   (e) adding sulfuric acid to the aqueous solution of step (d) to form monoethanolamine bisulfate;
   (f) heating the aqueous solution comprised of the monoethanolamine bisulfate of step (e) to yield 2-aminoethyl hydrogen sulfate ester;
   (g) reacting the 2-aminoethyl hydrogen sulfate ester of step (f) with a sulfite salt in an aqueous solution to yield taurine, wherein the sulfite salt is selected from the group consisting of ammonium, lithium, sodium, potassium, and a mixture thereof; and
   (h) separating the taurine of step (g) by solid-liquid separation.

8. The process of claim 7, wherein the solvent is selected from the group consisting of methanol, ethanol, propanol, isopropanol, tert-butanol, butanol, isobutanol, sec-butanol, dimethyl carbonate, tetrahydrofuran, dioxane, and a mixture thereof.

9. The process of claim 7, wherein the solvent is methanol.

* * * * *